United States Patent [19]

Matsui et al.

[11] Patent Number: 6,096,894
[45] Date of Patent: Aug. 1, 2000

[54] PRODUCTION METHOD OF 2-(P-ALKYLPHENYL)PYRIDINE COMPOUND

[75] Inventors: Kozo Matsui; Yoshihide Umemoto; Kiyoshi Sugi; Tetsuya Shintaku; Nobushige Itaya, all of Osaka, Japan

[73] Assignee: Sumika Fine Chemicals Co., Ltd., Osaka, Japan

[21] Appl. No.: 09/361,749

[22] Filed: Jul. 27, 1999

[30] Foreign Application Priority Data

Jul. 29, 1998 [JP] Japan .................................. 10-213702
Jul. 13, 1999 [JP] Japan .................................. 11-199557

[51] Int. Cl.$^7$ .............................................. C07D 213/127
[52] U.S. Cl. .............................................. 546/349
[58] Field of Search .............................................. 546/348

[56] References Cited

U.S. PATENT DOCUMENTS 5,288,895  2/1994  Bousset et al. .
5,723,621  3/1998  Shibata et al. .......................... 546/339
5,922,898  7/1999  Miller et al. .

FOREIGN PATENT DOCUMENTS

WO 97/40029  10/1997  WIPO .

OTHER PUBLICATIONS

Patent Abstracts of Japan, Abstract of JP 08 109143 (Asahi Glass Co., Ltd.) (1996).
1999 American Chemical Society (ACS), vol. 131, Issue 17, Abstract of JP 03 095157 (1999).
Gosmini et al., "Electrochemical Cross–Coupling Between 2–Halopyridines and Aryl or Heteroaryl Halides Catalysed by Nickel–2,2'–Bipyridine Complexes," *Tetrahedron*, 54, 1289–1298 (1998).
Hitchcock et al., "Selectivity in Palladium (0)–Catalyzed Cross–Coupling Reactions: Application to a Tandem Stille Reaction," *Tetrahedron Letters*, 36 (50),9085–9088(1995).
Negishi et al., "A Regiospecific Synthesis of Carbosubstituted Heteroaromatic Derivatives Via Pd–Catalyzed Cross Coupling," *Heterocycles*, 117–122 (1982).

*Primary Examiner*—Patricia L. Morris
*Attorney, Agent, or Firm*—Leydig, Voit & Mayer, Ltd.

[57] ABSTRACT

A method of producing a 2-(p-alkylphenyl)pyridine compound economically, easily and industrially, which comprises adding manganese dioxide and trimethylchlorosilane, or adding manganese chloride to an organic ether solvent, and reacting p-alkylphenylmagnesium halide and 2-halopyridine in the obtained organic ether solvent.

2 Claims, No Drawings

PRODUCTION METHOD OF 2-(P-ALKYLPHENYL)PYRIDINE COMPOUND

TECHNICAL FIELD OF THE INVENTION

The present invention relates to a production method of a 2-(p-alkylphenyl)pyridine compound. More particularly, the present invention relates to a production method of a 2-(p-alkylphenyl)pyridine compound, comprising reacting p-alkylphenylmagnesium halide and 2-halopyridine in an organic ether solvent in the presence of manganese chloride or a compound obtained from manganese dioxide and trimethylchlorosilane.

BACKGROUND OF THE INVENTION

A 2-(p-alkylphenyl)pyridine compound is useful as a pharmaceutical intermediate; for example, as a synthesis intermediate for 4-(pyridin-2-yl)benzaldehyde which is an intermediate for an anti-HIV drug (A) of the following formula disclosed in WO97/40029.

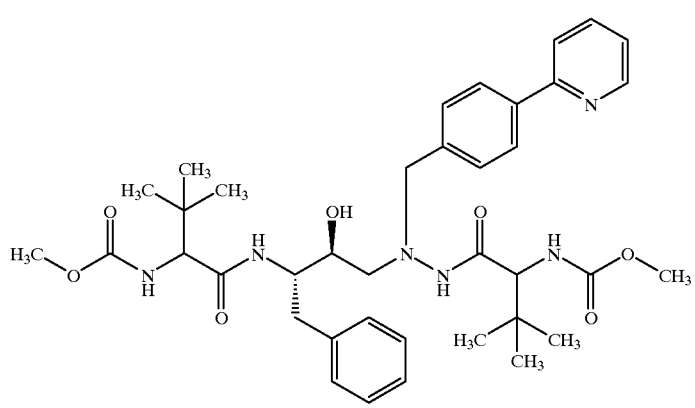

(A)

In addition, Japanese Patent Unexamined Publication No. 95157/1991 discloses a butenoic acid derivative as an agent for the therapy, prophylaxis and amelioration of ischemic heart disease. This butenoic acid derivative is synthesized via 4-(pyridin-2-yl)benzaldehyde. The above-mentioned 4-(pyridin-2-yl)benzaldehyde is synthesized by, for example, a method comprising brominating 2-(p-tolyl) pyridine and reacting the resultant compound with hexamine.

The production method of 2-phenylpyridine compound is disclosed in, for example, *Heterocycles*, vol. 18, 117–122 (1982), wherein 2-bromopyridine and phenylzinc chloride are reacted using $Pd(PPh_3)_4$ as a catalyst to give 2-phenylpyridine in an 89% yield. Moreover, the production method of 2-(p-alkylphenyl)pyridine compound is disclosed in, for example, *Tetrahedron Letters*, vol. 36, No. 50, 9085–9088 (1995), wherein a 2-arylpyridine compound (e.g., 2-(p-tolyl)pyridine) is obtained via an organic tin compound in a 60% yield again using $Pd(PPh_3)_4$ as a catalyst. *Tetrahedron*, vol. 54, 1289–1298 (1998) discloses that a 2-arylpyridine compound can be obtained by reacting arylzinc halide obtained electrochemically and 2-halopyridine using a nickel complex catalyst. However, the catalysts used in the production methods of these known 2-(p-alkylphenyl)pyridine compounds are expensive. Thus, there has been a demand of a production method of a 2-(p-alkylphenyl)pyridine compound that permits economical, facilitated and industrial production.

It is therefore an object of the present invention to provide a method of producing a 2-(p-alkylphenyl)pyridine compound economically, easily and industrially.

SUMMARY OF THE INVENTION

Such object can be achieved by the present invention, wherein manganese dioxide and trimethylchlorosilane are added, or manganese chloride is added to an organic ether solvent, and p-alkylphenylmagnesium halide and 2-halopyridine are reacted to give a 2-(p-alkylphenyl) pyridine compound economically, easily and industrially.

Accordingly, the present invention provides the following.

① A method of producing a 2-(p-alkylphenyl)pyridine compound of the formula (3)

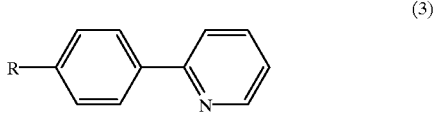

(3)

wherein R is alkyl having 1 to 4 carbon atoms, which comprises the steps of (a) adding manganese dioxide and trimethylchlorosilane, or adding manganese chloride to an organic ether solvent, and (b) reacting p-alkylphenylmagnesium halide of the formula (1)

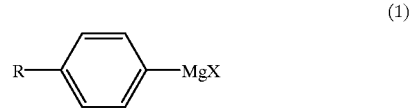

(1)

wherein R is as defined above and X is a halogen atom, with 2-halopyridine of the formula (2)

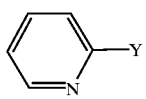

wherein Y is a halogen atom.

② The production method of the 2-(p-alkylphenyl)pyridine compound of ① above, wherein X and Y are chlorine atoms and R is methyl.

DETAILED DESCRIPTION OF THE INVENTION

The present invention is explained in detail in the following.

The alkyl having 1 to 4 carbon atoms at R may be linear or branched and is exemplified by methyl, ethyl, propyl, isopropyl, butyl and tert-butyl, with preference given to methyl.

The halogen atom at X is exemplified by chlorine and bromine, and is preferably chlorine.

The halogen atom at Y is exemplified by chlorine and bromine, and is preferably chlorine.

The 2-(p-alkylphenyl)pyridine compound can be produced by adding manganese dioxide and trimethylchlorosilane, or manganese chloride to an organic ether solvent, adding 2-halopyridine at once or portionwise, and adding a solution of p-alkylphenylmagnesium halide in an organic ether solvent to promote the reaction. The solution of p-alkylphenylmagnesium halide in an organic ether solvent is preferably added dropwise.

2-Halopyridine is exemplified by 2-chloropyridine and 2-bromopyridine, which is preferably 2-chloropyridine from the economical aspect.

p-Alkylphenylmagnesium halide is exemplified by p-tolylmagnesium chloride, p-tolylmagnesium bromide, p-ethylphenylmagnesium chloride, p-ethylphenylmagnesium bromide, p-propylphenylmagnesium chloride, p-propylphenylmagnesium bromide, p-butylphenylmagnesium chloride, p-butylphenylmagnesium bromide and the like, with preference given to p-tolylmagnesium chloride.

p-Alkylphenylmagnesium halide can be prepared in the same manner as in the usual preparation of Grignard reagent. Alkyl and halogen atom of p-alkylhalobenzene used for the preparation are the same as those of p-alkylphenylmagnesium halide.

p-Alkylphenylmagnesium halide is used in an amount of 0.5–2.0 moles, preferably 0.6–1.5 moles, per mole of 2-halopyridine.

When manganese dioxide and trimethylchlorosilane are used as the catalyst, manganese dioxide is used in an amount of about 0.01–0.3 mole, preferably about 0.02–0.2 mole, per mole of 2-halopyridine, for economical and reactivity reasons. The amount of trimethylchlorosilane to be used is preferably about 3 to 5-fold moles relative to 1 mole of manganese dioxide.

When manganese chloride alone is used as a catalyst, it is used in an amount of about 0.01–0.3 mole, preferably about 0.02–0.2 mole, per mole of 2-halopyridine, for economical and reactivity reasons.

The organic ether solvent is exemplified by tetrahydrofuran (THF). It may be a mixed solvent with other organic solvent as long as it is used in an amount that does not inhibit the reaction. Other usable organic solvent is a solvent that does not have reactivity with Grignard reagent, such as toluene.

The amount of the organic ether solvent to be used is not particularly limited and is preferably 2.5 to 10-fold amount by weight relative to 2-halopyridine.

The reaction temperature is preferably 0° C. to the boiling point of the solvent, more preferably 20° C.–75° C.

The reaction atmosphere is not particularly limited, but is preferably an inert gas atmosphere such as nitrogen gas atmosphere.

The reaction time varies depending on the reaction conditions such as reaction temperature, which is generally about 2–10 hours.

The completion of the reaction can be confirmed by, for example, high performance liquid chromatography.

The objective 2-(p-alkylphenyl)pyridine compound can be isolated by washing, extraction, filtration, concentration, distillation, crystallization and the like, whereby a 2-(p-alkylphenyl)pyridine compound or a salt thereof can be obtained.

The 2-(p-alkylphenyl)pyridine compound obtained by the method of the present invention is useful as an intermediate for the synthesis of 4-(pyridin-2-yl)benzaldehyde which is an intermediate for an anti-HIV drug (A) and disclosed in WO97/40029. For example, 2-(p-tolyl)pyridine is brominated and reacted with hexmine to give 4-(pyridin-2-yl) benzaldehyde.

The present invention is explained in detail by illustrative examples, to which the present invention is not limited in any way.

EXAMPLE 1

In a 2 L flask were added THF (213 g), manganese dioxide (5.43 g) and trimethylchlorosilane (27.1 g) and the mixture was left at room temperature for 12 hours, which was followed by addition of 2-chloropyridine (70.85 g). A solution (389.5 g) of p-tolylmagnesium chloride in THF, which was prepared from p-chlorotoluene (98.8 g), was added dropwise to the above-mentioned flask at 48–51° C. over 8 hours. After the completion of the reaction, partial THF was distilled away under reduced pressure at 40–50° C. and toluene (282 g) was added, which was followed by dropwise addition of water (550 ml).

Ammonium chloride (100 g) was added to the mixture and the resultant mixture was stirred. The insoluble material was filtrated. The filtrate was separated into an aqueous layer and an organic layer, and the aqueous layer was removed. To the organic layer were added water (300 ml) and conc. hydrochloric acid (53.0 g). After stiring, the mixture was stood still to separate the organic layer from the aqueous layer. To the organic layer were added water (150 ml) and conc. hydrochloric acid (4.0 g). After stirring, the mixture was stood for separation. The organic layer was discarded and the aqueous layer was combined with the previously-obtained aqueous layer. Thereto were added toluene and 25% aqueous sodium hydroxide (87.7 g) to make the aqueous layer alkaline. The small amount of insoluble material was removed by filtration and the filtrate was separated into an aqueous layer and an organic layer, and the aqueous layer was removed. The organic layer was concentrated. The concentrate contained 2-(p-tolyl)pyridine in a 75 mol % yield from 2-chloropyridine, as determined by HPLC. Distillation under reduced pressure gave the objective 2-(p-tolyl)pyridine in a 71% yield as a highly pure liquid.

IR(neat)cm$^{-1}$; 1615,1588,1563,1515,1467,1433,1299, 1185,1153,1111,989,830,773; $^1$H-NMR(CDCl$_3$) δ: 2.40(s, 3H), 7.19(m, 1H), 7.28(d, J=8.0 Hz, 2H), 7.70(d, J=1.6 Hz, 1H), 7.72(m, 1H), 7.89(d, J=8.0 Hz, 2H), 8.67(dt, J=2.0 Hz, 1.2 Hz, 1H) bp: 120–140° C./5–10 mmHg

EXAMPLE 2

1 L flask was charged with THF (213 g), manganese chloride (6.3 g, pulverized product) and 2-chloropyridine (70.85 g). A solution (330 g) of p-tolylmagnesium chloride in THF, which was prepared from p-chlorotoluene (104.3 g), was added dropwise to the above-mentioned flask at 47–58° C. over 7 hours. After the completion of the reaction, THF was distilled away under reduced pressure at 40–50° C. and toluene (282 g) was added, which was followed by dropwise addition of water (550 ml).

Ammonium chloride (100 g) was added to the mixture and the resultant mixture was stirred. Insoluble material was filtrated. The filtrate was separated into an aqueous layer and an organic layer, and the aqueous layer was removed. To the organic layer were added water (300 ml) and conc. hydrochloric acid (53.0 g). After stirring, the mixture was stood still to separate the organic layer from the aqueous layer. To the organic layerwere added water (150 ml) and conc. hydrochloric acid (4.0 g). After stirring, the mixture was stood for separation. The organic layer was discarded and the aqueous layer was combined with the previously-obtained aqueous layer. Thereto were added toluene and 25% aqueous sodium hydrogencarbonate (87.7 g) to make the aqueous layer alkaline. The small amount of insoluble material was removed by filtration. The filtrate was separated into an aqueous layer and an organic layer, and the aqueous layer was removed. The organic layer was concentrated. The concentrate contained 2-(p-tolyl)pyridine in a 60.4 mol % yield from 2-chloropyridine, as determined by HPLC. Distillation under reduced pressure gave the objective 2-(p-tolyl)pyridine in a 56% yield as a highly pure liquid.

The obtained 2-(p-tolyl)pyridine had the same spectrum data as obtained in Example 1.

EXAMPLE 3

2 L flask was charged with THF (227.1 g), manganese chloride (20.1 g, pulverized anhydrous product) and 2-chloropyridine (227.1 g). A solution (483.4 g) of p-tolylmagnesium chloride in THF, which was prepared from p-chlorotoluene (151.9 g), was added dropwise to the above-mentioned flask at 58–62° C. over 4 hours.

After the completion of the reaction, the reaction mixture was poured into a different 2 L flask containing water (1 L) and the pH of the aqueous layer was adjusted to 4 with conc. hydrochloric acid. The temperature was raised to about 55° C. and, after standing and separation, the aqueous layer was discarded. Distillation of the organic layer gave THF and 2-chloropyridine which contained a small amount of THF. Thus, 47.8% of 2-chloropyridine was recovered from the amount used. In addition, a 2-(p-tolyl)pyridine fraction (174.8 g) partially containing 4,4'-dimethylbiphenyl was obtained. The 2-(p-tolyl)pyridine fraction was subjected to acid-alkali purification comprising dissolving 2-(p-tolyl) pyridine in an acidic water, removing 4,4'-dimethylbiphenyl (neutral substance) into an organic layer and neutralizing the aqueous layer to purify 2-(p-tolyl)pyridine, whereby 157.3 g of 2-(p-tolyl)pyridine was obtained (yield: 88.9% from consumed 2-chloropyridine).

The obtained 2-(p-tolyl)pyridine had the same spectrum data as obtained in Example 1.

According to the present invention, a 2-(p-alkylphenyl) pyridine compound can be produced economically, easily and industrially. The obtained 2-(p-alkylphenyl)pyridine compound is useful as a synthesis intermediate for 4-(pyridin-2-yl)benzaldehyde which is an intermediate for an anti-HIV drug (A) and disclosed in WO97/40029. For example, 4-(pyridin-2-yl)benzaldehyde can be obtained by brominating 2-(p-tolyl)pyridine and reacting the resulting compound with hexamine. Consequently, a pharmaceutical intermediate for an anti-HIV drug and the like can be provided economically and easily.

This application is based on patent application Nos. 213702/1998 and 199557/1999 filed in Japan, the contents of which are hereby incorporated by reference.

What is claimed is:

1. A method of producing a 2-(p-alkylphenyl)pyridine compound of the formula (3)

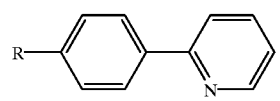

(3)

wherein R is alkyl having 1 to 4 carbon atoms, which comprises the steps of (a) adding manganese dioxide and trimethylchlorosilane, or adding manganese chloride to an organic ether solvent, and (b) reacting p-alkylphenylmagnesium halide of the formula (1)

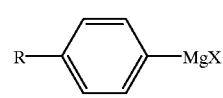

(1)

wherein R is as defined above and X is a halogen atom, with 2-halopyridine of the formula (2)

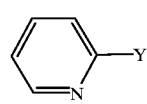

(2)

wherein Y is a halogen atom.

2. The production method of the 2-(p-alkylphenyl) pyridine compound of claim 1, wherein X and Y are chlorine atoms and R is methyl.

* * * * *